(12) United States Patent
Kaufhold

(10) Patent No.: US 6,452,016 B1
(45) Date of Patent: Sep. 17, 2002

(54) PROCESS FOR THE PREPARATION OF 1,2,3,6-TETRAHYDRO-2,2,6,6-TETRAMETHYLPYRIDINE N-OXIDE

(75) Inventor: Manfred Kaufhold, Marl (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 426 days.

(21) Appl. No.: 09/040,276

(22) Filed: Mar. 18, 1998

(30) Foreign Application Priority Data

Mar. 18, 1997 (DE) .......................... 197 11 226

(51) Int. Cl.$^7$ ...................... C07D 211/94; C07D 211/92
(52) U.S. Cl. .................. 546/348; 546/184; 546/242
(58) Field of Search .......................... 546/348

(56) References Cited

FOREIGN PATENT DOCUMENTS

| DE | 283864 | 4/1915 |
|----|--------|--------|
| EP | 0 574 667 | 12/1993 |
| GB | 1199351 | 7/1970 |

OTHER PUBLICATIONS

Eduard G. Rozantsev, et al., Institute of Chemical Physics, Academy of Sciences of the USSR, pp. 190 to 202, "Synthesis and Reactions of Stable Nitroxyl Radicals I. Synthesis", Apr. 1, 1971.

Par D. Bordeaux, et al., Acta Cryst., pp. 1656 to 1659, "Synthése De Radicaux Libres Nitroxydes Dérivés Du Tétraméthyl–2,2,6,6 Tétrahydropyridine–1,2,3,6; Structure De L'Epoxy–3,4 Tétraméthyl–1–2,2,6,6 Pipéridine–oxyle, $C_9H_{16}NO_2$", 1983.

*Primary Examiner*—Alan L. Rotman
(74) *Attorney, Agent, or Firm*—Oblon, Spivak, McClelland, Maier & Neustadt, P.C.

(57) ABSTRACT

The invention relates to a process for the preparation of 1,2,3,6-tetrahydro 2,2,6,6-tetramethylpyridine N-oxide by the catalytic oxidation of 1,2,3,6-tetrahydro-2,2,6,6-tetramethylpyridine, wherein 1,2,3,6-tetrahydro-2,2,6,6-tetramethylpyridine is oxidized with hydrogen peroxide in an aqueous medium in the presence of an alkaline earth metal salt or hydroxide as catalyst. The product is a polymerization inhibitor for monomers.

15 Claims, No Drawings

PROCESS FOR THE PREPARATION OF 1,2,3,6-TETRAHYDRO-2,2,6,6-TETRAMETHYLPYRIDINE N-OXIDE

BACKGROUND OF THE INVENTION

Field of the Invention

The invention relates to a process for the preparation of 1,2,3,6-tetrahydro-2,2,6,6-tetramethylpyridine N-oxide (hereafter called dehydro-TEMPO=DH-TEMPO) by the catalytic oxidation of 1,2,3,6-tetrahydro-2,2,6,6-tetramethylpyridine (THTMP).

DISCUSSION OF THE BACKGROUND

Syntheses of N-oxides by the oxidation of corresponding secondary amines are known from the literature. They differ principally in the oxidizing agent used. Thus, R. Winter and R. Malherbe carry out the oxidation with organic hydroperoxides, e.g. tert-butyl hydroperoxide (EP-A-0 157 738). They use an expensive oxidizing agent and obtain at least stoichiometric amounts of tert-butanol as a by-product. Percarboxylic acids, which are often recommended as oxidizing agents, also suffer from the same disadvantages. For example, Chou et al. use 3-chloroperoxybenzoic acid as the oxidizing agent (J. Org. Chem. 39 [1947], 2356, 2360).

On the other hand, the use of hydrogen peroxide as the oxidizing agent is appreciably more favorable because it is inexpensive and only water is formed as the by-product. D. P. Young and Rozantsev et al. recommend hydrogen peroxide as the oxidizing agent and a tungstic acid salt as catalyst (GB 1 199 351 and Tetrahedron 20 [1964], 131, 137). The disadvantages of this process are the extremely long reaction times of several days and the problem of disposing of the catalyst, which for reasons of environmental protection is not allowed to enter the waste water. Excessively long reaction times are required when using sodium carbonate as catalyst (Soviet Physics Doklaay 261, 1, [1981], 103, 110). Although the use of phosphotungstic acid as catalyst considerably shortens the reaction time, the catalyst is expensive to manufacture and the problem of disposal in an environmentally acceptable manner still remains (R. Briere, H. Lemaire and A. Rassat, Bull. Soc. Chim. France 11 [1965], 3273).

All the oxidation processes mentioned above share the fact that they consume a large amount of chemicals, are technically expensive, create waste disposal problems and/or require long reaction times, which is economically impractical.

These disadvantages are overcome by the process according to EP O 574 667, wherein 2,2,6,6-tetrarnethyl-piperidine is oxidized with hydrogen peroxide as the oxidizing agent and alkaline earth metal salts as catalysts.

SUMMARY OF THE INVENTION

It has now been found, surprisingly, that the olefinically unsaturated 1,2,3,6-tetrahydro-2,2,6,6-tetrarnethylpyridine N-oxide can also be advantageously prepared by the catalytic oxidation of 1,2,3,6-tetrahydro-2,2,6,6-tetramethylpyridine if 1,2,3,6-tetrahydro-2,2,6,6-tetramethylpyridinn presence of an alkaline earth metal salt or hydroxide as catalyst.

The reaction is represented by the following equation:

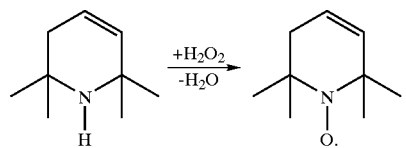

In the process according to the invention, THTMP is oxidized by hydrogen peroxide in the presence of alkaline earth metal salts or hydroxide as catalysts to give the corresponding N-oxide, DH-TEMPO, with a very high selectivity of over 90%. Surprisingly, in the process according to the invention, the olefinic double bond is not attacked either in the THTMP or in the DH-TEMPO.

BRIEF DESCRIPTION OF THE PREFERRED EMBODIMENTS

Various other objects, features and attendant advantages of the present invention will be more fully appreciated as the same becomes better understood from the following detailed description of the preferred embodiments, which is not intended to be limiting unless otherwise specified.

It had to be expected that the double bond in the THTMP or DH-TEMPO would react with hydrogen peroxide since this is precisely what is described in DE-OS 28 38 364 for the preparation of 2,2,6,6-tetramethylpiperidine-3,4-diol. However, and surprisingly, in the process according to the invention, even excesses of hydrogen peroxide do not lead to a significant reaction of the double bond.

DH-TEMPO is an outstanding polymerization inhibitor for monomers such as acrylic acid and its esters, because it scavenges radicals which initiate polymerization, even in the gas phase. It exhibits a favorable combination of desirable properties for this use:

1. As a liquid with a low solidification point, it is easy to handle. TEMPO, by contrast, has an m.p. of 35° C. and is therefore liquid or solid according to the ambient conditions.
2. It is readily soluble in hydrocarbons such as toluene.
3. It has a higher vapor pressure than the 4-substituted derivatives according to EP 0 574 667, which is favorable for use as an inhibitor in the gas phase.

DH-TEMPO is also very suitable as a redox catalyst.

Preferable catalysts in the present invention are salts and hydroxides of calcium, strontium, barium and especially magnesium, e.g. the chlorides, sulfates, nitrates, phosphates, formates, acetates, etc. A prerequisite is that the salts or hydroxides are at least partially soluble in the reaction mixture at the reaction temperatures and to this extent are present in the reaction mixture extensively in ionic form. The salts or hydroxides can be used as solids, as a mixture of solids or in the form of a suspension or solution of a solid or several solids. Of course, it is also possible to use alkaline earth metal compounds which react with components of the reaction mixture, e.g. hydrolyze, and then dissociate into ions, examples being alkaline earth metal alcoholates and Grignard compounds. The metals themselves can also be used because they react with water under the reaction conditions.

It is surprising and advantageous that even low concentrations of alkaline earth metal salt are totally sufficient to achieve the high yields of the process according to the invention. Good results are obtained when the concentration of alkaline earth metal ions is as low as 0.002 molar. Suitable alkaline earth metal salts include magnesium sulfate heptahydrate, magnesium chloride hexahydrate and magnesium nitrate hexahydrate. The molar ratio of THTMP to alkaline earth metal salt or hydroxide is normally $10^5:1$ to 10:1, preferably $10^5:1$ to $10^2:1$ and especially about $10^4:1$. Because these amounts are small, the catalyst consumption is low; in addition, alkaline earth metal salts and hydroxides are inexpensive and environmentally benign substances. Calcium and magnesium compounds, in particular, are widespread in nature, so small amounts of such salts in the waste products of the process do not have a significant impact on the environment.

The reaction is carried out in an aqueous medium, i.e. in water or with the concomitant use of a water-miscible inert organic solvent. When stirred with water, THTMP forms an emulsion which reacts in this form with hydrogen peroxide. Solvents increase the solubility of the THTMP; they generally increase the reaction rate and shorten the reaction times. For economic reasons, the solvents used are preferably lower alcohols or diols such as methanol, ethanol, n- or iso-propanol, ethylene glycol or propylene glycol. Solvents with a low vapor pressure are preferred on safety grounds because they cannot form explosive mixtures with the oxygen-rich off-gas. Preferred solvents are high-boiling diols or diol ethers such as ethylene glycol, propylene glycol, ethylene glycol monoalkyl or dialkyl ethers, propylene glycol monoalkyl or dialkyl ethers, polyethylene glycols, polyethylene glycol monoalkyl or dialkyl ethers, polypropylene glycols and polypropylene glycol monoalkyl or dialkyl ethers.

Hydrogen peroxide can be used in the commercially available forms as a 10% to 60% by weight solution.

THTMP is prepared from the corresponding saturated alcohol, 4-hydroxy 2,2,6,6-tetramethylpiperidine, by the elimination of water using methods known from the literature (E. Fischer, Ber. 16, 1604; Ber. 17, 1790, the entire contents of which are hereby incorporated by reference).

In practice, the process is preferably carried out e.g. as follows: THTMP, catalyst, water and optionally a solvent are placed in a vessel, the amount by weight of water advantageously being 0.1 to 2 times, preferably 0.3 to 0.8 times, the amount by weight of THTMP. The amount by weight of solvent, if used, is advantageously 0.1 to 2 times the amount by weight of water used. The temperature of this mixture is advantageously adjusted to 0 to 100° C., preferably to 40 to 90° C. The hydrogen peroxide is added over 0.1 to 2 hours and the reaction mixture is advantageously stirred for a further 1 to 30 hours, preferably 5 to 15 hours, at the chosen temperature. Alternatively the addition of the hydrogen peroxide can be interrupted one or more times so that any hydrogen peroxide still present is used up first. The molar ratio of THTMP to hydrogen peroxide is advantageously 1:1 to 1:10, preferably 1:1 to 1:5 and especially 1:1.5 to 1:2.5. The course of the reaction can be monitored by gas chromatographic analysis.

The reaction mixture is worked up by conventional methods, which in most cases is very simple because the THTMP is almost completely converted. For example, after a reaction without organic solvent, the reaction mixture is simply worked up by distillation of the water under vacuum. The residue which remains is DH-TEMPO with a purity of over 95% as determined by gas chromatography. As the catalyst concentration is normally less than 0.1% pm, it does not need to be separated off for most applications. Of course, the reaction mixture can also be worked up by extraction and the extract purified by various washing procedures. This variant is particularly recommended when a high-boiling solvent has been used. For many purposes the extract can be used directly without further purification, an example being a solution in toluene.

EXAMPLES

Having generally described this invention, a further understanding can be obtained by reference to certain specific examples which are provided herein for purposes of illustration only and are not intended to be limiting unless otherwise specified.

Example 1

A glass apparatus is used which consists of a three-necked round-bottomed flask equipped with a stirrer, a thermometer and a dropping funnel, and the following ingredients are used:

| | |
|---|---|
| 70.0 g (0.5 mol) | of 1,2,3,6-tetrahydro-2,2,6,6-tetramethylpyridine (= THTMP) |
| 50.0 g | of water |
| 0.4 g | of magnesium sulfate heptahydrate |
| 72.9 g | of hydrogen peroxide (30% by weight) |

The THTMP, water and magnesium sulfate heptahydrate are placed in the flask and the mixture is heated to 70° C., with stirring. The hydrogen peroxide is added dropwise over 2 hours. The mixture is subsequently stirred for 3 hours, a further 27.0 g of hydrogen peroxide are then added and the mixture is left to react, with stirring. After a postreaction time of 7 hours at 70° C., the N-oxide content is ca. 80%. Two further additions of 25.0 g of hydrogen peroxide with postreaction times of 2 hours after each addition increase the N-oxide content to 97.2%.

To decompose excess hydrogen peroxide, the reaction mixture is stirred first at 80° C. and then at 90° C. for half an hour at each temperature. The mixture is then cooled and the phases are separated to give 71.0 g of organic phase.

To separate off unreacted THTMP, the organic phase is washed with 10% sulfuric acid and neutralized with solid sodium bicarbonate. The purity (GC analysis) is 99%. The calculated yield is 91.3% of theory, based on the amount of THTMP used. The solidification point of the liquid red-colored DH-TEMPO is −10°C.; it is miscible with toluene in all proportions. The product has the abovementioned combination of favorable properties.

Examples 2 to 4

The apparatus described in Example 1 is used, the amounts of THTMP, water and hydrogen peroxide given in Example 1 are used and 0.02 mol of each of the following magnesium compounds is added as catalyst:

magnesium hydroxide magnesium chloride magnesium nitrate

The procedure is as described in Example 1 and the results obtained are very similar.

Example 5

The apparatus described in Example 1 is used, the amounts of THTMP and magnesium sulfate heptahydrate given in Example 1 are used and a mixture of 30.0 g of polyethylene glycol (molecular weight ca. 2000) and 20 g of water is added instead of pure water. The reaction proceeds appreciably faster and is complete after 7 hours. The hydrogen peroxide consumption of 95 g is considerably smaller than in Example 1. Work-up is carried out by extraction with toluene; the yield is 92.5%.

Having now fully described the invention, it will be apparent to one of ordinary skill in the art that many changes and modifications can be made thereto without departing from the spirit or scope of the invention as set forth herein.

This application is based on German patent application No. 197 11 226.9, filed Mar. 18, 1997, the entire contents of which are hereby incorporated by reference.

What is claimed as new and desired to be secured by Letters Patent of the United States is:

1. A process for the preparation of 1,2,3,6-tetrahydro-2,2,6,6-tetramethylpyridine N-oxide by the catalytic oxidation of 1,2,3,6-tetrahydro-2,2,6,6-tetramethylpyridine, comprising oxidizing 1,2,3,6-tetrahydro-2,2,6,6-tetramethylpyridine with hydrogen peroxide in an aqueous medium in the presence of an alkaline earth metal salt or hydroxide as catalyst.

2. The process as claimed in claim 1 wherein the alkaline earth metal salt is an alkaline earth metal salt selected from the group consisting of chlorides, sulfates, nitrates, phosphates, formates, and acetates, and mixtures thereof.

3. The process as claimed in claim 1 wherein the alkaline earth metal salt or hydroxide comprises an alkaline earth metal selected from the group consisting of calcium, strontium, barium, and magnesium, and mixtures thereof.

4. The process as claimed in claim 3 wherein, the alkaline earth metal salt or hydroxide is magnesium hydroxide or a magnesium salt.

5. The process as claimed in claim 4 wherein the magnesium salt is selected from the group consisting of magnesium sulfate heptahydrate, magnesium chloride hexahydrate, and magnesium nitrate hexahydrate, and mixtures thereof.

6. The process as claimed in claim 1 wherein a molar ratio of the 1,2,3,6-tetrahydro-2,2,6,6-tetramethylpyridine to the alkaline earth metal salt or hydroxide ranges from $10^5$:1 to 10:1.

7. The process as claimed in claim 6 wherein a molar ratio of the 1,2,3,6-tetrahydro-2,2,6,6-tetramethylpyridine to the alkaline earth metal salt or hydroxide ranges from $10^5$:1 to $10^2$:1.

8. The process as claimed in claim 1 wherein the reaction is carried out in an aqueous emulsion.

9. The process as claimed in claim 1, further comprising an organic solvent.

10. The process as claimed in claim 9, wherein the organic solvent comprises a high-boiling diol or diol-ether.

11. The process as claimed in claim 10 wherein the high-boiling diol or diol-ether is selected from the group consisting of ethylene glycol, propylene glycol, an ethylene glycol monoalkyl or dialkyl ether, a propylene glycol monoalkyl or dialkyl ether, polyethylene glycol, a polyethylene glycol monoalkyl or dialkyl ether, polypropylene glycol, and polypropylene glycol monoalkyl or dialkyl ether, and a mixture thereof.

12. The process as claimed in claim 1 wherein the reaction is carried out at a temperature of 0–100° C.

13. The process as claimed in claim 12 wherein the reaction is carried out at a temperature of 40–90° C.

14. The process as claimed in claim 1, further comprising working up and separating 1,2,3,6-tetrahydro-2,2,6,6-tetramethylpyridine N-oxide.

15. A redox catalyst which includes the 1,2,3,6-tetrahydro-2,2,6,6-tetramethylpyridine N-oxide prepared by the process as claimed in claim 1.

* * * * *